United States Patent [19]

Schwehr et al.

[11] Patent Number: 4,475,072

[45] Date of Patent: Oct. 2, 1984

[54] PATIENT-POSITIONING X-RAY TABLE

[75] Inventors: Gregory D. Schwehr, Milwaukee; Richard T. Brandt, New Berlin; James J. Kandler, Milwaukee, all of Wis.

[73] Assignee: General Electric Company, Milwaukee, Wis.

[21] Appl. No.: 441,301

[22] Filed: Nov. 12, 1982

[51] Int. Cl.³ .................... G05B 19/28; H01J 37/20
[52] U.S. Cl. .................................... 318/602; 318/9; 318/54; 318/280; 269/323; 378/17; 378/209
[58] Field of Search .................. 318/3, 9, 10, 14, 15, 318/602, 280, 54; 269/323; 378/209, 17

[56] References Cited

U.S. PATENT DOCUMENTS

| | | | |
|---|---|---|---|
| 3,805,080 | 4/1974 | Yager et al. | 269/323 |
| 3,806,109 | 4/1974 | Weber et al. | 378/209 |
| 3,822,875 | 7/1974 | Schmedemann | 378/209 X |
| 3,868,103 | 2/1975 | Pageot et al. | 378/209 X |
| 4,013,019 | 3/1977 | Horsey | 378/209 X |
| 4,112,303 | 9/1978 | Brandt | 378/17 |
| 4,115,695 | 9/1978 | Kelman | 378/17 |
| 4,144,455 | 3/1979 | Lutz | 269/323 |
| 4,197,464 | 4/1980 | Amor | 269/323 |
| 4,392,096 | 7/1983 | Grajewski et al. | 318/625 |

Primary Examiner—B. Dobeck
Attorney, Agent, or Firm—Alexander M. Gerasimow; Douglas E. Stoner

[57] ABSTRACT

An X-ray table having an elevator mounted on a base for vertical movement, an intermediate support mounted on the elevator for moving longitudinally, and a carriage with a patient cradle on it for moving longitudinally on the support. A pair of gas springs mounted at the forward end of the table provides a constant upward force to compensate for weight of the elevator and the cantilevered load which is exerted as the patient cradle is extended in the longitudinal direction. There are individual servomotors for driving the support and the cradle. The intermediate support drive includes a drive bar and switch assemblies for sensing any force of more than 25 lbs., for example, exerted on the patient or patient cradle and for disengaging the servodrives in response thereto. The cradle drive incorporates a zero-backlash longitudinal friction drive which includes a harmonic drive unit to achieve accurate positioning of the patient. An encoder is driven by a closed-loop cable attached to the patient cradle to accurately indicate its position and speed even though there is a two-stage drive.

11 Claims, 11 Drawing Figures

PATIENT-POSITIONING X-RAY TABLE

CROSS REFERENCE TO RELATED APPLICATION

This patent application is related to commonly assigned U.S. patent application Ser. No. 311,687, (now U.S. Pat. No. 4,392,096) filed Oct. 15, 1981, and which is incorporated herein by reference.

BACKGROUND OF THE INVENTION

This invention relates to an improved dual motor, single-axis position and velocity servo system for a patient-supporting table that is used to position a patient in an x-ray beam in computed axial tomography and in computed projection radiography apparatus, for example.

As is known, in one type of computed axial tomography apparatus, an x-ray source is mounted on a scanner base that is journaled for rotation about a nominally horizontal axis on a tiltable gantry. A multiple cell x-ray detector is mounted on the scanner base on the opposite side of the axis from the x-ray source. The x-ray beam emanating from the source is collimated into a fan-shaped configuration that spreads over the circumferential length of the detector and is thin in the direction to which the rotational axis of the scanner base is perpendicular. The patient who is to be examined is customarily supported on an x-ray-transmissive table top or cradle in coincidence with the rotational axis of the scanner. The cradle must be supported from a floor-mounted base in a fashion that allows it to be moved in what is called the axial or longitudinal direction relative to the base so that the x-ray beam may be caused to penetrate successive layers of the body. The base also includes an elevator mechanism for adjusting the vertical position of the cradle relative to the gantry. As is well known, the computed axial tomography process requires orbiting the x-ray source and detector jointly about the patient so that the detector will be able to produce analog signals representative of x-ray beam attenuation by the patient for a multiplicity of x-ray source and detector positions that are attained in a 360° orbit in one direction or the other. As is well known, the signals representative of beam attenuation are variously processed with a computer system that yields digital data representative of the intensity of the picture elements that comprise cross-sectional image of the body layer that has been scanned. The picture element data is converted to analog video signals and is used to display the image on the display screen of a video monitor.

The gantry allows the scanner to be tilted so that the fan-shaped x-ray beam, instead of being projected perfectly vertically, is projected at an angle relative to the horizontal axis to permit imaging angular rather than vertical body layers. Pre-existing computed axial tomography apparatus typically provided for tilting the plane of the fan-shaped beam through an angular range of about 15° from either side of vertical. Since the gantry is a large upright structure, when tilted through a small angle such as 15°, its bottom swings out toward the base on which the axially movable patient-supporting cradle is mounted, but the base can be set far enough away from the gantry to avoid having the latter strike the base. This is so because the x-ray-transmissive cradle supports the patient in cantilever fashion from the base. However, in a more advanced computed axial tomography apparatus design, tilting of the gantry by as much as 20° from either side of vertical has been provided for. Thus, the base that supports the cradle must be set farther away from the gantry to avoid interference by the base when the gantry is tilted through the larger angular range. Hence, in the new design, it became necessary to increase the distance through which the patient is translated axially relative to the base. It would be possible to lengthen the cradle so a major part of the patient could be advanced into the x-ray beam but, since the patient would be supported in cantilever fashion, intolerable deflection of the cradle would result. The alternative, disclosed and claimed in the aforementioned patent application, that was adopted is to make the patient-supporting table assembly in two sections comprised of an intermediate support or carriage that moves relative to the base and a patient cradle mounted on the intermediate support for moving axially relative to it. The intermediate support and cradle are driven by individual servomotors which are sequentially activated and controlled so as to transport the patient-supporting cradle at a constant overall velocity and, if desired, to stop the movement at predetermined positions to enable imaging of desired anatomical features.

In connection with the computed projection radiography method, using the apparatus described briefly above, the x-ray source and detector are held in a fixed position rather than being orbited to perform a scan as in the computed axial tomography method. In this method, the patient must be advanced through the fan-shaped x-ray beam at a very constant velocity for undergoing a line-by-line scan with a fan beam that is about 1.5 mm thick, for example. As the patient is being advanced, the x-ray detector cells yield analog signals corresponding to x-ray attenuation at closely successive positions of the patient on a line-by-line basis, and the resulting attenuation data is stored until the length of the body which is of interest has been scanned. A computer then uses the attenuation data to produce digital data representative of the intensities of the picture elements for all scan lines, and these signals are used to drive a video monitor which displays a visual image corresponding to the projected x-ray image. In effect, the computed projection radiography method yields a visual x-ray image that is comparable to the image obtained with ordinary radiographic film but with greater contrast than is obtainable with film, because the dynamic range of the x-ray detector is usually greater than that of film.

The inventive x-ray table disclosed herein includes unique structural features which enhance the operating characteristics thereof and which provide desirable safety features as compared to conventional patient-positioning devices. One structural feature is a zero-backlash longitudinal friction drive for moving a patient cradle so as to enable accurate positioning of the patient for scanning. A safety feature is provided in that the driving friction between the drive unit and the patient cradle is proportional to the weight of the patient. In this manner, the driving force can never exert more pressure to the patient than the coupling friction, unlike the torque of the drive, as in most systems, which is designed for the heaviest load. This drive also incorporates a pivot which proportions the weight of the patient between a drive roller and an idler roller and provides compensation for unavoidable flex in the patient cradle. This system also eliminates the need for expensive and noisy gear rack, ball-and-screw drive, belt, or chain drives used in the past to achieve zero backlash. Another safety device which is provided senses any force more than 25 lbs, for example, exerted on either the patient or patient support in a longitudinal direction, and disengages the servomotors. The force may be exerted by the drive, gantry, or other outside agency. Longitudinal position accuracy is obtained by the use of an encoder attached to the cradle by a closed-loop cable system which records the total patient longitudinal motion, even though there is a two-stage drive. Since the encoder is not placed in the drive mechanism, but senses actual cradle motion, it can very accurately indicate cradle position and speed. Another important feature of the improved x-ray table is the use of a pair of gas springs mounted at the gantry end of the x-ray table to exert an upward force on the front end of the table to compensate for the cantilevered load which is exerted as the patient is extended in the longitudinal direction. The upward force exerted by the gas springs reduces the loading on the elevator drive mechanism and permits smooth and quiet operation. The gas springs also compensate for the weight of the elevation mechanism and are less bulky and complicated than previously used counterbalance devices.

It is, therefore, an object of the invention to provide an improved x-ray table which enables the accurate positioning of the patient for scanning.

It is another object of the invention to provide an x-ray table having features to enhance the safety of the patient.

It is still another object of the invention to provide an x-ray table to very accurately indicate the position and speed of the patient support so as to ensure high image quality.

It is a further object of the invention to provide an x-ray table which is less bulky and complex and which operates in a smooth and quiet manner.

SUMMARY OF THE INVENTION

An x-ray-table system includes a base, and an elevator mounted on the base for moving vertically relative thereto. An elongated support is mounted to the elevator for moving longitudinally relative to the base, while an elongated cradle is mounted on the support means for moving longitudinally relative to the support. A reversible driving motor and means for coupling the motor to the support are provided to selectively drive the support between a retracted position and an advanced position and again back to the retracted position. Similarly, a reversible cradle-driving motor and means for coupling the motor to the cradle are provided to selectively move the cradle between a retracted position and an advanced position, and then back to the retracted position relative to the support. A pair of gas springs is mounted to the base and to the elevator so as to exert a constant upward force against the elevator plate to thereby reduce the load on a ball-and-screw drive used for raising and lowering the elevator.

Among the other features of the x-ray table are a longitudinal friction drive for driving the cradle with the aid of a harmonic drive unit, an encoder attached to the patient support by a closed-loop cable system and which records the total patient-longitudinal motion even though there is a two-stage drive, and a support drive assembly which includes a U-shaped member and a pair of switch assemblies which are used to sense a force exceeding a predetermined limit exerted either on the patient or the cradle in a longitudinal direction and to disengage the drive.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
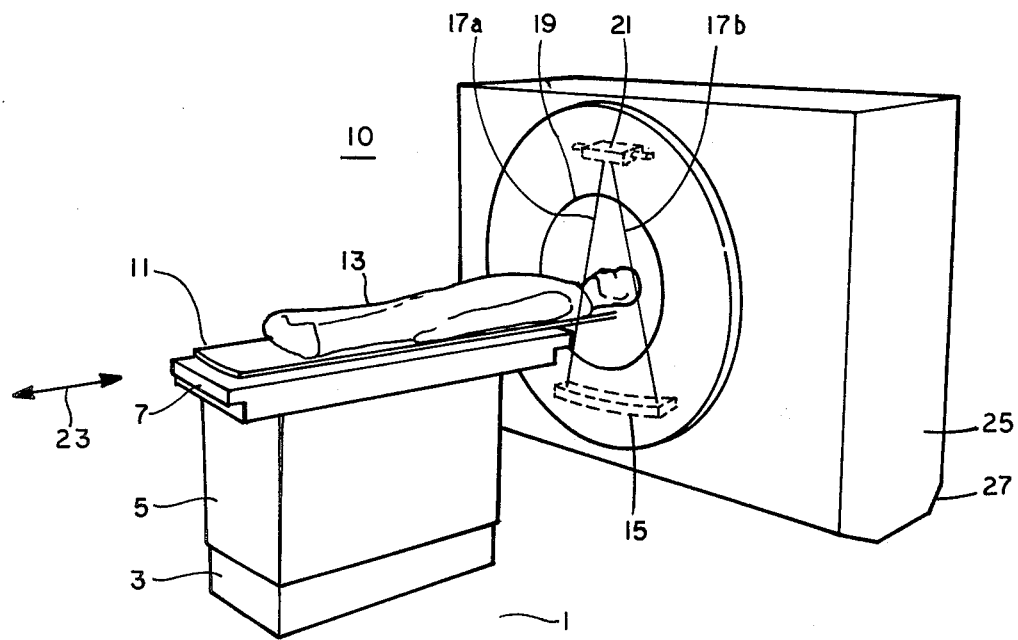
FIG. 1 is a perspective view of a typical computed axial tomography and computed projection radiography apparatus, together with the new x-ray table assembly with which the scanner cooperates.

FIG. 1 illustrates a typical apparatus suitable for performing computed axial tomography and computed projection radiography. The apparatus is designated generally by the numeral 10 and includes a housing 25 supported from within by a gantry which is not visible in FIG. 1, but the details of which may be ascertained by reference to U.S. Pat. Nos. 4,112,303 and 4,115,695, both of which are assigned to the same assignee as the present invention, and both of which are incorporated herein by reference. The gantry is instrumental in tilting the housing from the vertical position when the apparatus is used as a computerized tomography scanner to image body sections at an angle. By way of example, the housing may be tilted as much as 20° in either direction from vertical in the illustrated design. The lower corners or edges 27 of the housing are slanted so the housing will not strike the floor when it is tilted. Essential components of the apparatus are an x-ray source 21 and a multi-cell x-ray detector 15. The source and detector are mounted on a scanner base, not visible, which is journaled for rotation so that the x-ray source and the detector can orbit jointly about the horizontal axis when a computed axial tomography scan is being performed. The apparatus has a circular opening 19 that is centered on a horizontal axis 23 to provide a passageway for advancing and retracting a patient 13, supported by a patient cradle 11, relative to a fan-shaped x-ray beam whose boundaries are marked 17a and 17b. This beam is collimated so that it is typically between about 2.6 mm and 17 mm thick in a direction perpendicular to the plane of the x-ray beam.

When performing computed axial tomography, the patient is advanced longitudinally in steps so that successive transverse layers of the body may be scanned by joint orbiting of x-ray source 21 and detector array 15 while attenuation data is obtained from the detector for permitting reconstruction of an x-ray image in a vertical section of the body. When the apparatus is used for performing computed projection radiography, x-ray source 21 and detector 15 are locked against rotation, and the patient is advanced at a very constant speed through the x-ray beam, since the cells in the x-ray detector that provide the attenuation data must be read out at constant time intervals. In this manner, the computer, not shown, can relate the body position to the attenuation data and produce an image on a television screen, not shown, representative of a projection of the body that is essentially shadow-graph.

The components of the x-ray table assembly are identified generally in FIG. 1 and are represented schematically. The assembly includes a base 3 positioned on a floor 1 and having mounted thereon an elevator portion 5 which is movable vertically with respect to the floor. A first carriage or intermediate support 7 is mounted on elevator portion 5 in a fashion that permits it to be moved longitudinally, that is, parallel to the axis of rotation 23 of the scanner, as well as in a vertical direction. A patient cradle 11, made substantially of x-ray-transmissive material, is mounted on intermediate support 7 for longitudinal movement in opposite directions relative thereto. The intermediate support and cradle are driven longitudinally in that order to advance a patient 13 in the forward direction toward circular opening 19 in housing 25. They are driven in opposite order to move the patient rearwardly, that is, away from the housing.

Figure 2:
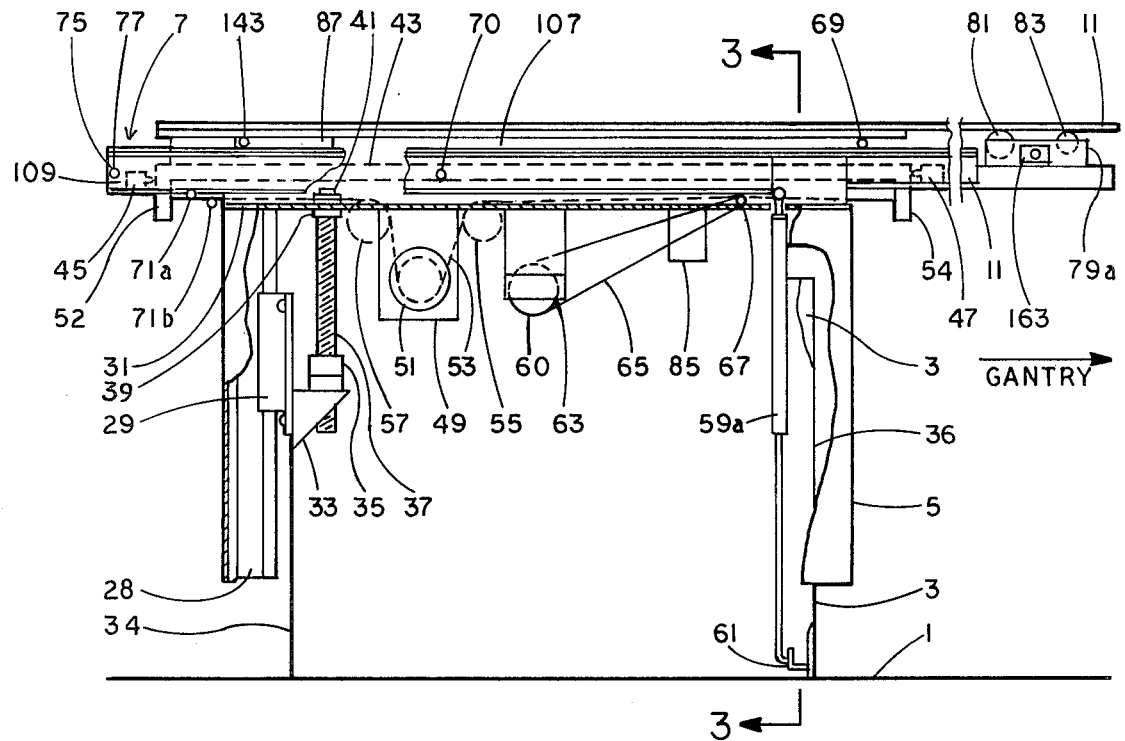
FIG. 2 is a side-elevation view of the table assembly with parts broken away to reveal internal structures in the base and elevator.
Figure 3:
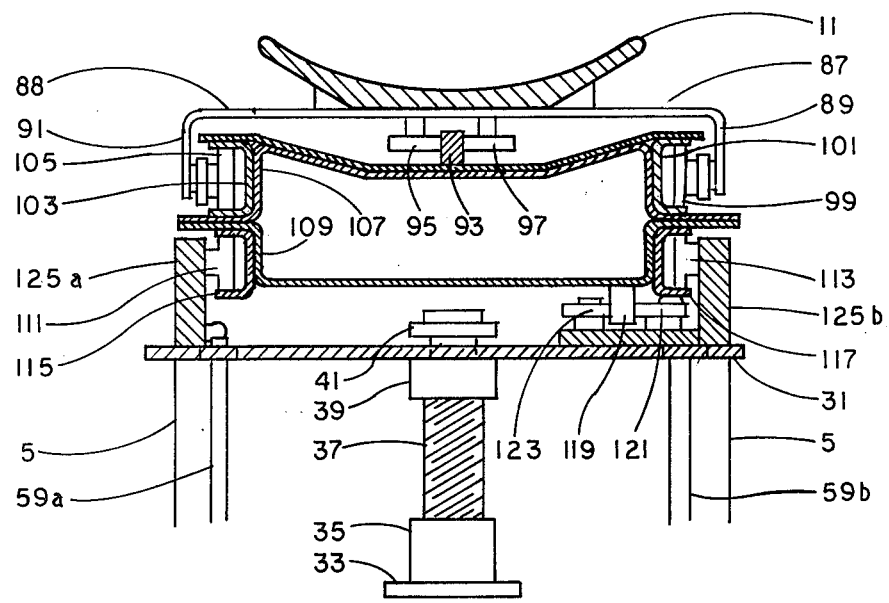
FIG. 3 is a vertical section through the table taken on a line corresponding with 3—3 in FIG. 2.
Figure 6:
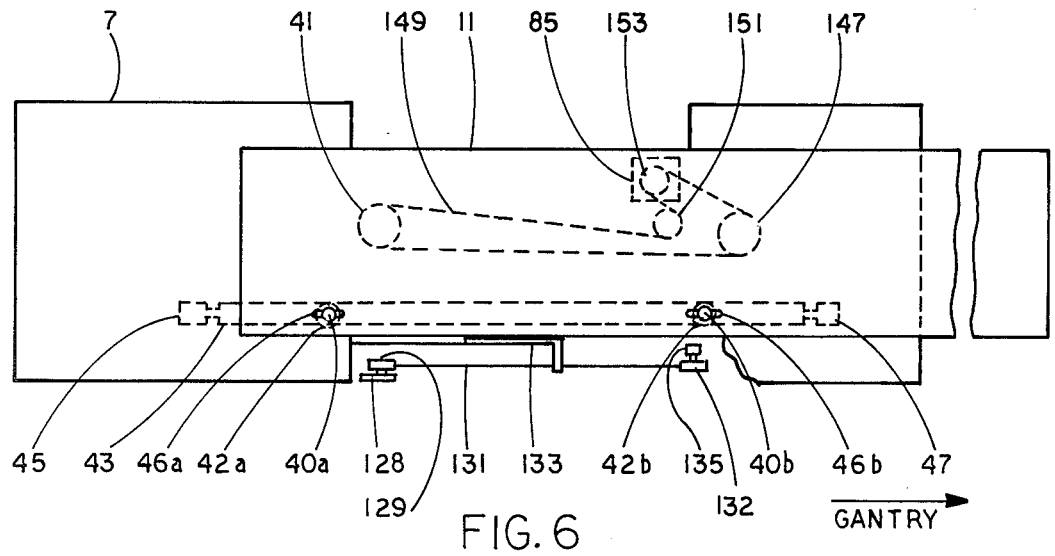

The more detailed description of the mechanical features of the patient-supporting table assembly may be best understood if initial reference is made to FIGS. 2, 3, and 6. In FIG. 2, it may be seen that elevator 5 is positioned for vertical movement on floor-mounted base 3 with the aid of a ball-and-screw drive. The ball-and-screw drive is made up of a screw element 37 and a ball element 35 internally threaded to accept the lower end of screw 37. Ball element 35 is attached to a rear wall 34 of base 3 with the aid of a bracket 33. Screw 37 is attached at its upper end to the underside of a top plate 31, forming part of elevator 5, with the aid of a cup 39 containing a bearing (not shown). A drive sprocket 41 is attached to screw 37 on the other side of cup 39. Although FIG. 2 shows only a single ball-screw drive at the rear wall of the base, it is to be understood that there is another one longitudinally spaced from it and mounted to front wall 36 of the base. The manner in which elevator 5 is moved vertically relative to the base with the aid of an elevator motor 85 will be understood if reference is made to FIG. 6 which illustrates a plan view of the x-ray table assembly. In FIG. 6, there is shown, in addition to drive sprocket 41, already described, a second drive sprocket 147 associated with the ball-and-screw drive (not visible) attached to the front base wall. There is also shown an idler sprocket 151 and a drive sprocket 153 driven by elevator motor 85 mounted to the underside of elevator top-plate 31 (FIG. 2). A drive chain 149 interconnects the various sprockets, and when driven by the motor, causes rotation of the screw elements in each ball-and-screw drive thereby raising or lowering the elevator. Elevator 5 is provided with lateral support by means of a bushing 29 (FIG. 2) mounted to rear wall 34 of the base and a rail 28 mounted to the adjacent rear wall of the elevator. The bushing may be of the type known as a Thompson linear bushing.

Excessive loading of the ball-and-screw drives is avoided by a pair of gas springs provided near front wall member 36 of the base. One such spring 59a is shown in FIG. 2 as attached at its lower end by means of a bracket 61 to front wall member 36, and at its upper end to elevator top plate 31. Reference to FIG. 3 will indicate that a second gas spring 59b substantially identical to spring 59a and laterally spaced therefrom is also provided. Gas springs have the property of exerting a substantially constant force regardless of the degree of compression, so that springs 59a and 59b exert a constant force against elevator plate 31 to reduce the loading on the ball-and-screw drives when the cradle holding a patient weighing as much as 300 pounds is in the fully extended position. As described before, the gas springs also compensate for the weight of the elevator and are less bulky and complicated than the previously used counterbalanced devices. Due to the reduced loading, the ball-and-screw drives operate in a smooth and quiet manner. Typically, each spring is selected to exert a constant force of approximately 250 pounds on the elevator plate. Such gas springs are available commercially from the Gas Spring Corporation of Colmar, Pa., for example. Application Ser. No. 282,897, (now U.S. Pat. No. 4,366,577) assigned to the same assignee as the present invention, discloses the use of gas springs to bring about constant deceleration of a rotating scanner base.

Reference is made again to FIG. 2 wherein it may be seen that the intermediate support 7 is made up of two elongated frame members 107 and 109. These frame members are joined with each other and are adapted to translate jointly relative to floor-mounted base 3 under the influence of a servomotor which will be identified and discussed later. Referring to FIG. 3, it may be seen that there is a pair of channels 115 and 117 fastened to the sides of intermediate support 7. These channels serve as tracks for a plurality of rollers such as those marked 111 and 113 which are journaled for rotation on columns 125a and 125b, for example. The columns are mounted to top plate 31 of elevator 5. Thus, it will be evident that the intermediate support 7 can translate to base 3 on a set of rollers 111 and 113 toward and away from the viewer when looking at FIG. 3 and in the left and right directions when the viewer is looking at FIG. 2. It should be noted that there is a longitudinally extending guide bar 119 fastened to the bottom of frame member 109 of intermediate support 7. Bar 119 has a length substantially co-extensive with the length of intermediate support 7. The bar is captured between pairs of rollers such as those marked 121 and 123. The rollers are mounted to the top of elevator plate 31 for rotation about vertical axes, such that the rollers will cooperate with bar 119 to prevent lateral shifting of intermediate support 7.

Referring further to FIG. 3, it may be seen how a cradle carriage 87 is mounted on intermediate support 7 for independent longitudinal movement relative to the intermediate support. Cradle carriage 87 comprises a channel-like member having a flat top 88 and depending side flanges 89 and 91. A plurality of rollers such as those designated 99 and 105 are mounted for rotation on side flanges 89 and 91 within a longitudinally extending pair of channels 101 and 103 fastened to frame member 107. It will be evident that the channel member of the cradle assembly can thereby move longitudinally on intermediate support member 7. The curved x-ray-transmissive cradle 11, on which the patient is actually supported, is fastened to top 88 of the cradle carriage. As shown in FIG. 2, metallic cradle carriage 87 is much shorter than the x-ray-transmissive cradle 11, so that the metallic carriage never gets into the x-ray beam even when the cradle is fully extended relative to the intermediate support. By way of example, cradle 11 is a molded resin product selected to be highly transmissive to x-rays. Typically, cradle 11 is designed to support a patient weighing up to 300 pounds in cantilever fashion without the cradle deflecting objectionably. Excessive deflection would cause the x-ray-attenuation data to be inaccurate. It should be noted in FIG. 3 that cradle carriage 87 is provided with a pair of guide rollers such as those marked 95 and 97. These rollers capture a guide track 93 between them. Since the track is fastened to the intermediate support 7, rollers 95 and 97 run along the sides of track 93 to guide cradle carriage 87 in a straight line as it moves relative to the intermediate support.

Means for driving intermediate support 7 longitudinally have been omitted from FIG. 3 and will now be described in more detail with reference to FIGS. 2, 6, and 9.

As seen in FIG. 2, a servomotor 49 for driving intermediate support 7 in opposite longitudinal directions is mounted to the underside of elevator top plate 31 for vertical movement therewith. A sprocket 51 is fastened to one end of the shaft of servomotor 49. A chain 53 runs on sprocket 51 and over to a pair of idler sprockets 55 and 57 that are journaled on elevator 5. The chain continues in opposite directions from the idler sprockets with opposite ends of the chain terminated at clamps 48 and 50 (FIG. 9) which are fastened to depending flanges 52 and 54 of a U-shaped bar 43. As is best shown in FIGS. 6 and 9, bar 43 is attached to frame member 109 by means of a pair of shoulder bolts 40a and 40b passing through a pair of elongated slots 46a and 46b and held in place by washers 42a and 42b which also space bar 43 from frame member 109. It is important to note that, although the bar is attached to frame member 109, it is free to move within slots 46a and 46b formed in frame member 109. It will be evident that reversible servomotor 49 can thereby chain drive intermediate support 7 longitudinally in selected opposite directions.

Figure 9:
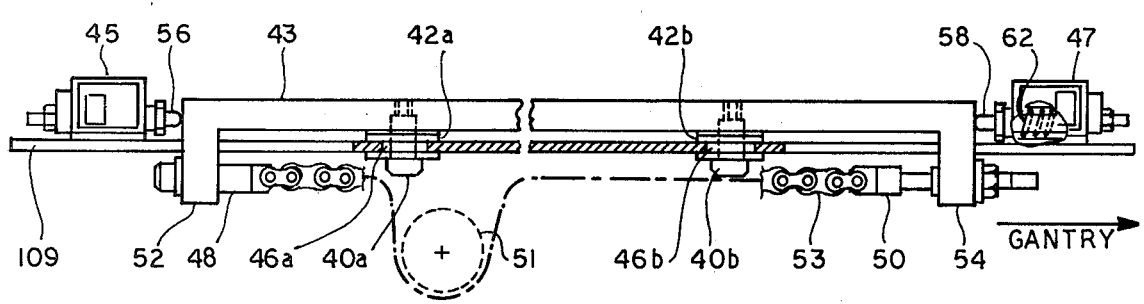
FIG. 9 is a front elevation view of an assembly used to drive the intermediate support and to sense any force exerted either on the patient or patient support in a longitudinal direction and for disengaging the servomotors.

In addition to providing the means for driving intermediate support 7 longitudinally in opposite directions, as described, U-bar 43 cooperates with switch assemblies 45 and 47 mounted on frame member 109 such that respective plungers thereof, 56 and 58, contact flanges 52 and 54 and center bar 43 at approximately the midpoint of slots 46a and 46b, as shown in FIGS. 6 and 9. In the event, for example, that the longitudinal motion of the intermediate support or the cradle is impeded in either direction, the switches act to de-energize the intermediate assembly drive and/or cradle drive (described hereinafter). The manner in which this feature operates will be described with reference to FIG. 9, and it will be assumed for the purpose of describing such operation that the movement of the intermediate support toward the gantry has been impeded. In this case, servomotor 49 continues to drive the U-bar against plunger 58 of switch assembly 47. Plunger 58 is prebiased by means of a spring 62 situated internal to assembly 47, as indicated in the cut-away view of switch assembly 47 in FIG. 9, to remain stationary until the pressure exerted by bar 43 against plunger 58 exceeds the tension on spring 62 which may be set to, for example, 25 pounds. Bar 43 then moves within the limits defined by slots 46a to produce a corresponding movement of plunger 58 so as to actuate an electrical switch (not shown separately) which disengages servomotor 49 and/or the cradle drive servomotor to prevent further movement of the intermediate support and the cradle. It will be appreciated that any obstruction in the movement of the intermediate assembly 7 in a direction away from the gantry will cause plunger 56 of switch assembly 45, which is similar in construction to switch assembly 47, to activate a second electrical switch which will again de-energize the servomotors.

Figure 4:
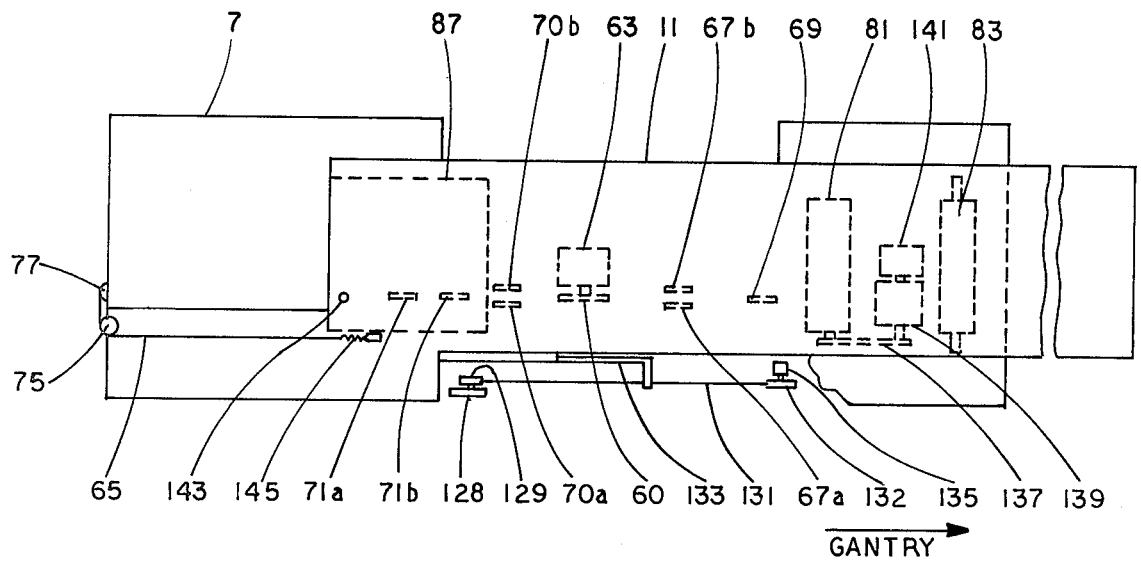
FIGS. 4 and 6 are plan views of the patient-supporting x-ray table assembly.

The longitudinal drive system for driving cradle carriage 87 and patient cradle 11 relative to intermediate support 7 is generally shown in FIGS. 2 and 4. The cradle drive system comprises a reversible servomotor 139 (FIG. 4) which is mounted to intermediate support 7. The longitudinal axis of the shaft of motor 139 is parallel to a large friction drive roller 81 which is journalled for rotation by means which will be described hereinafter. Drive roller 81 frictionally engages the bottom surface of that part of cradle 11 which extends away from cradle carriage 87. The driving friction between drive roller 81 and cradle 11 is proportional to the weight of the patient. This provides a safety feature since the driving force can not exert more pressure to cradle 11 than the coupling friction. An idler roller 83 provides support under cradle 11 at the outmost point possible on intermediate support 7 to minimize deflection when cradle 11 is extended in cantilever fashion relative to the intermediate support.

A detailed description of the drive system for driving the cradle carriage and the patient-support cradle, generally described above, will now be undertaken with reference to FIGS. 7, 8, 10, and 11.

Figure 7:
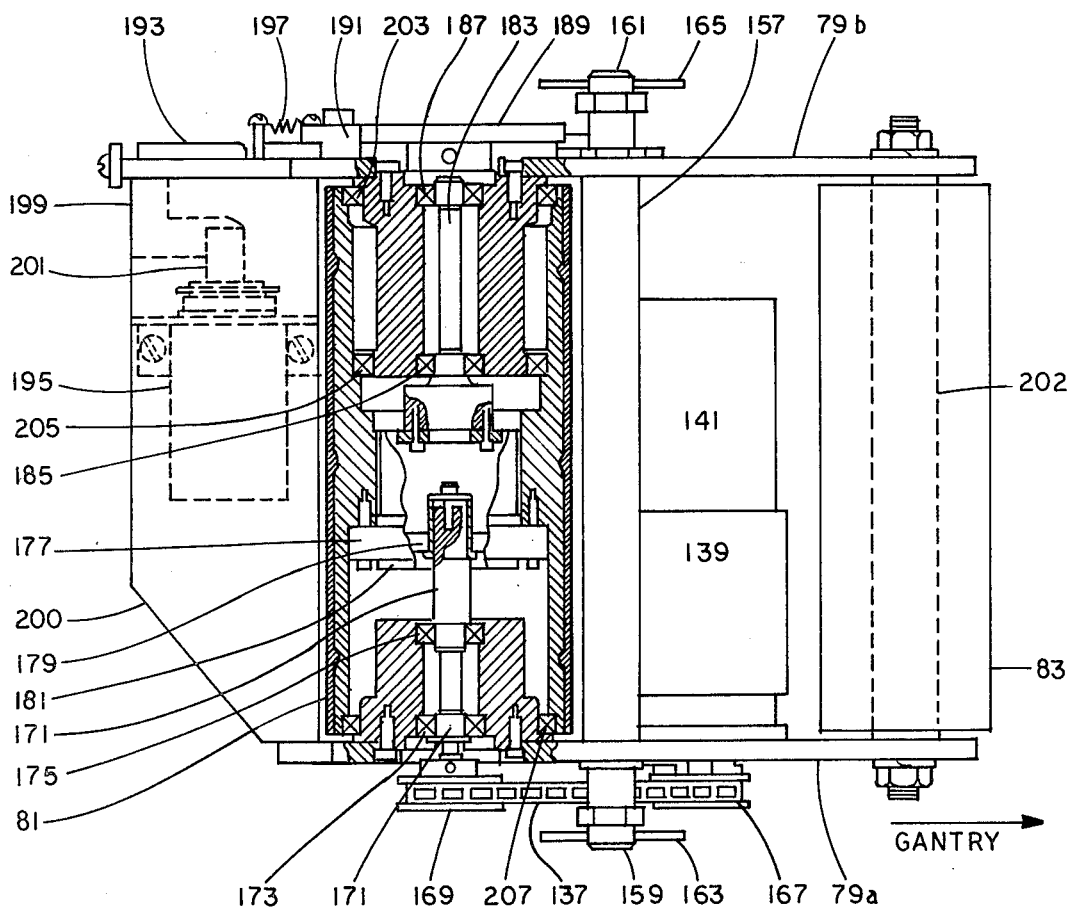
FIG. 7 is a plan view of the patient-support drive assembly with portions cut away to reveal details of the zero-backlash drive.

It is evident from FIG. 7 that the drive assembly is comprised of a pair of parallel frame members 79a and 79b between which friction-drive roller 81 and idler roller 83 are mounted. The frame members are held together at one end by a spacer plate 200 and at the forward end by an axle 202 around which idler roller 83 rotates. A centrally located spacer bar 157 provides additional support. The drive assembly is mounted to pivot on intermediate support 7 by means of pivot points 159 and 161 which extend outwardly from frame members 79a and 79b, respectively, substantially in alignment with spacer bar 157. Pivot points 159 and 161 rest on pivot brackets 163 and 165 which are fastened to the intermediate assembly as shown more clearly in FIG. 2. Returning to FIG. 7, it will be noted that the position of spacer bar 157 is selected such that 60% of the weight of the cradle and the patient thereon is applied to drive roller 81 and 40% to idler roller 83. The effect of the rocking motion resulting from pivots 159 and 161 being off center is to proportion the load on drive roller 81 and to provide compensation for flex in the patient support when it is fully extended. A servomotor 139 and tachometer 141 are mounted forwardly of drive roller 81 on frame member 79a. A toothed pulley 167 is mounted on the shaft of servomotor 139. A toothed belt 137 engages pulley 167 and a second toothed pulley 169 mounted on a shaft which engages a wave generator of a harmonic drive unit of the type generally disclosed in U.S. Pat. Nos. 2,906,143 and 3,415,143, and which is commercially available from United Shoe Machinery Company of Wakefield, Mass.

Figure 10:
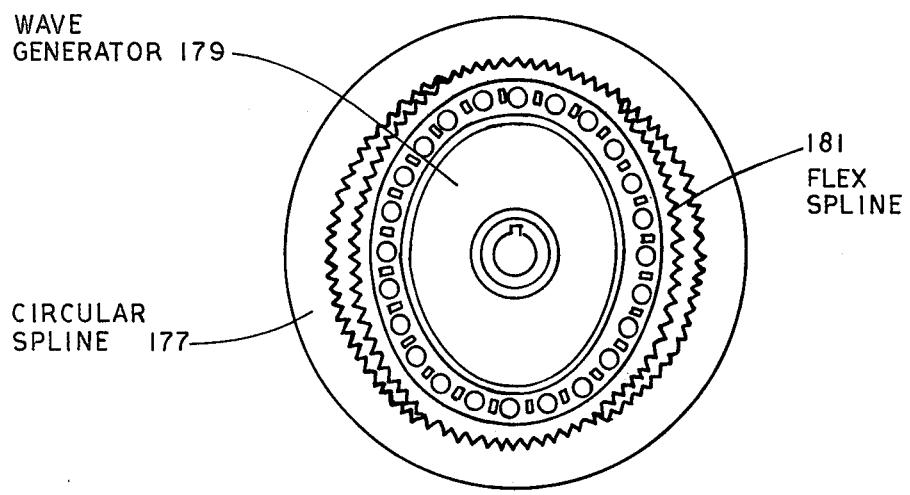
FIG. 10 is a schematic illustration of a harmonic drive unit used in the zero-backlash drive.
Figure 11:
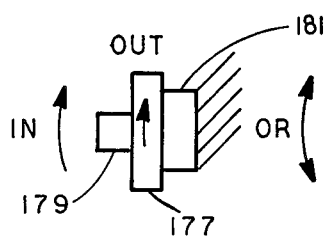
FIG. 11 depicts schematically the manner in which the elements of the harmonic drive unit are connected.

The basic operation of a harmonic drive unit will be described next so that its application (described more fully hereinafter) in the cradle drive system may be fully appreciated. FIG. 10 is a schematic illustration of a harmonic drive unit which includes a circular spline 177, a wave generator 179, and a flex spline 181. The circular spline is a rigid, thick-walled ring with internal splined teeth, while the flex spline is a non-rigid, cylindrical, thin-walled cup with two less splined teeth and on a smaller-pitched diameter than the circular spline. The wave generator is an elliptical ball-bearing assembly which includes an oldham-type shaft coupling. The flex spline assumes an elliptical shape upon insertion of the wave generator into the bore such that the flex-spline teeth engage with the circular-spline teeth at two points 180° apart to form a positive gear mesh. Various transmission functions may be obtained by varying the input, output, and fixed element. The particular configuration employed for driving the cradle carriage and the cradle is schematically illustrated in FIG. 11. The driving force is applied to wave generator element 179. Flex spline element 181 is held stationary, while the output is obtained through circular spline 177. In the event that the patient-supporting cradle must be retracted quickly, such as in the event of a medical emergency, the flex spline may be released so that drive roller 81 is then free to rotate along with circular spline 177.

Figure 8:
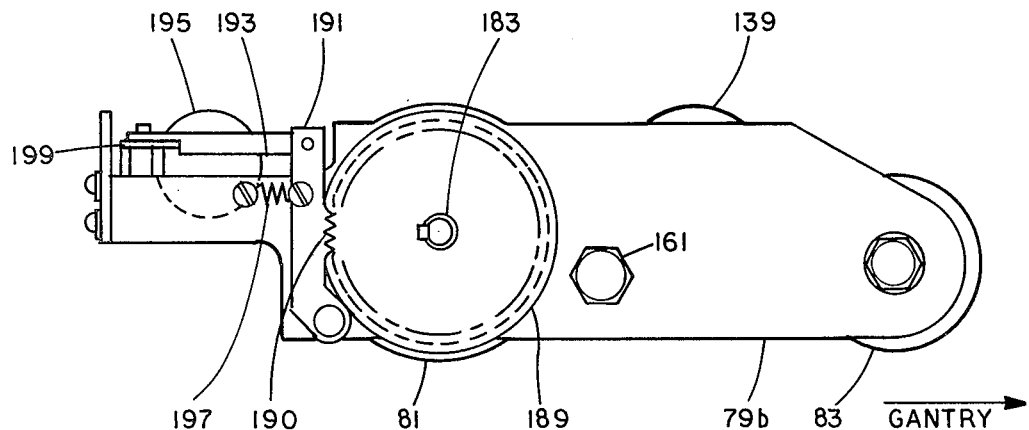
FIG. 8 is a side-elevation view of the patient-support assembly shown in FIG. 7.

Referring again to FIG. 7, in which harmonic drive unit elements are assigned the same reference numerals as in FIGS. 10 and 11, it is seen that roller drive pulley 169 is attached to a shaft 171 attached to wave generator 179. Shaft 171 is free to rotate by means of bearings 173 and 175. Flex spline 181 is coupled to a shaft 183 having a gear 189 affixed to the end thereof outside frame member 79b. As is best seen in FIG. 8, gear 189 is engaged and held against rotation by a rack 191 which is held in place by link elements 193 and 199 which are coupled to a plunger 201 (FIG. 7) of a solenoid 195 which is normally energized. Continuing with reference to FIG. 7, solenoid 195 is mounted on the underside of spacer plate 200. Circular spline 177 is attached to drive roller 81 and comprises the output element. Thus, as pulley 169 is driven by belt 137, the rotational motion of the wave generator 179 is transferred to circular spline 177 which then rotates drive roller 81 on bearings 203, 205, and 207. As previously described, drive roller 81 frictionally engages patient support 11 (FIG. 2) and drives it in a manner which eliminates backlash.

Under some circumstances, such as either an electrical power failure or a medical emergency, for example, it may be necessary to quickly retract the patient support so that the patient may be attended to. In the event of an electrical failure, normally energized solenoid 195 (FIG. 7) would be de-energized so that movement of plunger 201 results in rack 191 (FIG. 8) being disengaged from gear 189 by spring 197, thereby freeing shaft 183 to which flex spline 181 is attached, to rotate within bearings 185 and 187. As described before with reference to FIG. 11, this permits the free rotation of the flex spline 181 and circular spline 177 and, hence, drive roller 81 in the reverse direction. The patient support may thus be manually retracted with relative ease.

The general operating mode on the dual-carriage, extensible and contractable x-ray table assembly is described below. The detailed manner in which this is accomplished is described in U.S. patent application Ser. No. 311,687, previously incorporated herein by reference.

When the patient is to be translated from home position over base 3 forwardly into the x-ray beam as in FIG. 1, intermediate support 7 undergoes longitudinal driving motion first. The cradle carriage 87 (not visible in FIG. 1) and cradle 11 are just carried with the intermediate support at this time. The intermediate support is accelerated to a constant speed during a very short interval. It then travels a predetermined distance, and as soon as intermediate support 7 begins to decelerate, cradle drive motor 139 turns on and causes carriage 87 and its cradle 11 to accelerate relative to the intermediate support at the same rate that the intermediate support is decelerating relative to the base 3, so that the longitudinal speed of the intermediate support and cradle remains constant relative to the base on which they are supported. Intermediate support drive motor 49 is caused to stop simultaneously with the cradle drive motor 139 reaching its maximum and constant speed. Cradle motor 139 then continues to drive the cradle longitudinally at the same speed at which the intermediate support was formerly being driven. The cradle is then driven to a permissible, maximum limit in the longitudinal direction, whereupon it is decelerated at a controlled rate and stopped. Thus, the patient is now advanced through the x-ray-beam path. The table sections, namely, the intermediate support 7 and cradle 11, are operated in reverse sequence to retract the patient out of the path of the x-ray beam.

When the patient is to be retracted, cradle 11 is driven first, back to intermediate support 7, and next, the intermediate support is driven longitudinally until it reaches its home position. In the retraction process, the cradle is again driven to a point whereupon the deceleration of the cradle at a substantially linear rate starts and acceleration of the intermediate support at a corresponding rate starts. However, as in the case of forward motion described in the preceding paragraph, the intermediate support becomes accelerated to its maximum and constant speed at the end of the transition zone so that the patient continues to be moved at a constant speed.

In order to move the patient at a constant speed, it is necessary to know both the acceleration and position of each of intermediate support 7 and patient support 11.

The acceleration of intermediate support assembly 7 relative to base 3 is measured by a tachometer (not shown) coupled to the shaft of intermediate support drive motor 49 shown in FIG. 2. The acceleration of patient cradle 11 relative to the base is provided in a similar manner by tachometer 141 coupled to the shaft of cradle motor 139 (FIGS. 4 and 7).

The position of intermediate assembly 7 is detected by a pulley-and-wiper potentiometer arrangement shown in FIG. 4. A pulley 129 journaled for rotation to a bracket 128 and a potentiometer 135 are mounted to the top of elevator plate 31 (FIG. 1) in a spaced-apart relationship. A cord or cable 131 encircles pulley 129 and another pulley 132 mounted to the shaft of potentiometer 135, and is joined at its ends at a bracket 133 which is part of intermediate assembly 7 to form a loop. Thus, it is evident that, when the intermediate assembly moves, bracket 133 will move with it causing the potentiometer shaft to rotate so that the output signal from the potentiometer indicates the position of intermediate assembly 7.

Figure 5:
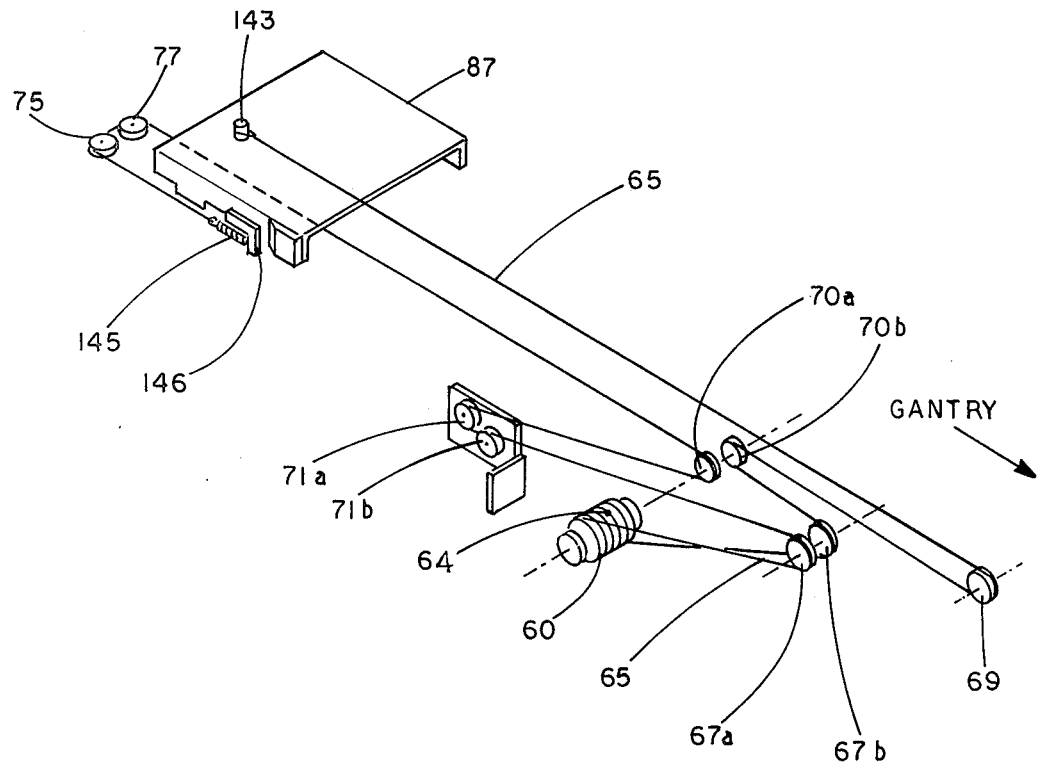
FIG. 5 is a perspective view of the closed loop encoder assembly.

The longitudinal position of cradle 11 is measured with an encoder 63 mounted on the underside of elevator plate 31 (FIG. 2). The encoder is driven by a closed-loop cable system, a perspective view of which is depicted in FIG. 5. The manner in which the closed-loop system is constructed will be best understood if, in addition to FIG. 5, reference is also made to FIGS. 2 and 4 which illustrate the pulley configuration and attachment points on the x-ray table assembly and in which like reference numerals are assigned to like parts. FIG. 4 depicts a top view of the pulley configuration, while FIG. 2 depicts a side view. Referring now to FIG. 5, one end of a cable 65 is attached to a pin 143 on the underside of cradle carriage 87, while the other end is attached to a bracket 146 on the side of the cradle carriage by means of a spring 145 which maintains the cable under tension. An intermediate point of cable 65 is fastened at, for example, a point 64 to a take-up pulley 60 to avoid slippage. Cable 65 sequentially engages pulleys 69 and 70b mounted on intermediate assembly 7, a pulley 67b attached to the top of elevator plate 31, winds around take-up pulley 60 attached to the shaft of encoder 63 (FIG. 4), and then returns to a pulley 67a mounted on elevator plate 31 adjacent to pulley 67b. From pulley 67a, the cable continues to a pair of pulleys 71a and 71b mounted at the rear of elevator 5 (as shown in FIG. 2) and then to a pulley 70a mounted adjacent to pulley 70b on the intermediate assembly. Thence, cable 65 continues around a pair of pulleys 77 and 75 at the rear of intermediate assembly 7 and terminates at spring 145.

As shown in FIGS. 2 and 5, when cradle carriage 87 moves to the left relative to the base 3 in FIG. 2, cable 65 rotates pulley 60 in one direction so that cable 65 unwinds at one side of the pulley and is taken up at the other. The rotation of pulley 60 then drives encoder 63 in one direction. Similarly, when cradle carriage 87 is driven to the right, encoder 63 rotates in the other direction. Encoder 63 is of a known type that is adapted to deliver electronic pulses which are counted to permit determining the position of cradle carriage 87 and, hence, cradle 11 relative to a stationary base 3. The encoder pulses are coded to provide an indication of the distance that the cradle has travelled longitudinally relative to fixed base 3. It should be evident that the encoder 63 will be driven at any time the cradle moves, that is, when the cradle moves as a result of the intermediate support 7 on which the cradle is carried being driven and as a result of the cradle being moved along the intermediate support. The manner in which the pulses from encoder 63 are used to regulate the speed of servomotors 49 (FIG. 2) and 139 (FIG. 4) is described in the patent application incorporated herein by reference.

From the foregoing, it will be appreciated that in accordance with the invention an improved x-ray table system is provided to enable the accurate transport and positioning of the patient for scanning so as to ensure high-image quality. The improved x-ray table is less bulky and complex and operates in a smooth and quiet manner. The x-ray table also includes features which enhance patient safety.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. An x-ray-table system comprising:
   a base;
   elevator means mounted on said base for moving vertically relative thereto;
   elevator drive means for raising and lowering said elevator means;
   an elongated support means mounted to said elevator for moving longitudinally;
   a reversible support means driving motor and means for coupling the motor to the support means for moving said support means selectively between a retracted position and an advanced position and back to a retracted position, relative to said elevator;
   elongated cradle means mounted to the support means for moving longitudinally relative to said support means;
   a reversible cradle means driving motor and means for coupling said motor to the cradle means for moving said cradle means selectively between a retracted position and an advanced position and back to a retracted position relative to said support means; and
   gas-spring means mounted at one of the ends thereof to said base and at the other end to said elevator means, said gas-spring means being adapted to exert a substantially constant force against said elevator means to thereby reduce the load on said means for raising and lowering said elevator means, particularly when at least one of said support-and-cradle means is in the advanced position.

2. The x-ray table of claim 1, wherein said elevator drive means comprises a pair of ball-and-screw-drive assemblies disposed at opposite ends of said elevator means, co-linearly with said support means and cradle means, and wherein said gas-spring means comprises a pair of gas springs each mounted to said base and to said elevator means adjacent to the one of said assemblies disposed nearest the end of said elevator means from which said support-and-cradle means depend when in the advanced position.

3. An x-ray-table system comprising:
   a base;
   elevator means mounted on said base for moving vertically relative thereto;
   elevator drive means for raising and lowering said elevator means;
   an elongated support means mounted to said elevator for moving longitudinally;
   a reversible support means driving motor and means for coupling the motor to the support means for moving said support means selectively between a retracted position and an advanced position and back to a retracted position, relative to said elevator;
   an elongated cradle means mounted to the support means for moving longitudinally relative to said support means;
   a reversible cradle means driving motor and means for coupling said motor to the cradle means for moving said cradle means selectively between a retracted position and an advanced position and back to a retracted position relative to said support means; and said means for coupling said cradle means driving motor to the cradle means, including a drive roller coupled to said cradle-driving motor, and an idler roller, said cradle means resting on said drive-and-idler rollers, such that said drive roller frictionally engages said cradle means for movement.

4. The x-ray table of claim 3, wherein said means for coupling said cradle-driving motor to said cradle means further comprises a pair of parallel frame members to which said drive-and-idler rollers are journalled, said last-mentioned coupling means including pivot means for supporting each of said frame members so as to distribute a greater fraction of the cradle-weight load on said drive roller than on said idler roller.

5. The x-ray table of claim 3, wherein said means for coupling said cradle-driving motor to said cradle means includes a harmonic drive means coupled at an input thereof to said cradle-driving motor and at an output thereof to said drive roller.

6. The x-ray table of claim 5, wherein said harmonic drive means is disposed on the interior of said drive roller and includes circular-spline, wave-generator, and flex-spline elements, said circular spline being secured to the interior of said drive roller and forming the output of said harmonic drive means, said wave generator being coupled to the drive shaft of said cradle-driving motor and forming the input to said harmonic drive means, and wherein said flex spline is coupled to a means adapted for selectively holding said flex spline against rotation when said cradle means is driven by said cradle-driving motor and for releasing said flex spline when said cradle means is to be moved without the aid of said cradle-driving motor.

7. The x-ray table of claim 6, wherein said means for holding said flex spline comprises:
 a gear secured to said flex spline;
 gear rack means for engaging said gear and holding it stationary;
 a solenoid having a retractable plunger; and
 linkage means for coupling said gear rack means to said plunger, such that in a first position of said plunger said gear rack means engages said gear, and in a second position of said plunger said gear rack is retracted allowing said flex spline and said drive roller to rotate freely.

8. The x-ray table of claim 3, wherein said means for coupling said support-driving motor to said support means comprises:
 an elongated member having depending flanges at opposite ends thereof; and
 a drive chain which operatively engages said supporting drive motor and which is attached at its ends to one of said flanges, said member being mounted to said support means for movement relative thereto within a predetermined range.

9. The x-ray table of claim 8, wherein said means for coupling said support-driving motor to said support means further comprises a pair of switch assembly means each having pre-biased actuator means, said switch assembly means being mounted to said support means opposite one another at opposite ends of said elongated member adjacent to said flanges such that collectively said actuators center said member within its predetermined range of movement, each of said switch assembly means being operable to disengage said support-and-cradle-driving motors when the movement of at least one of said support means and cradle means is impeded such that the force exerted by one of said flanges against the corresponding actuator means exceeds the bias thereon.

10. An x-ray-table system comprising:
 a base;
 elevator means mounted on said base for moving vertically relative thereto;
 elevator drive means for raising and lowering said elevator means;
 an elongated support means mounted to said elevator for moving longitudinally;
 a reversible support means driving motor and means for coupling the motor to the support means for moving said support means selectively between a retracted position and an advanced position and back to a retracted position, relative to said elevator;
 cradle-carriage means mounted to said support means for moving longitudinally relative thereto;
 elongated cradle means mounted to said cradle-carriage means and to said support means for moving longitudinally relative to said support means;
 a reversible cradle means driving motor and means for coupling said motor to said cradle for moving said cradle means selectively between a retracted position and an advanced position and back to a retracted position relative to said support means; and
 encoder means for providing an indication of the position of said cradle means relative to said base regardless of the position of said support means, said encoder means including cable means attached at one end to said cradle-carriage means and engaging sequentially: a first plurality of pulley means mounted to said support means, a second plurality of pulleys mounted to said elevator means, a take-up pulley coupled to an input shaft of said encoder means, a third plurality of pulleys mounted to said elevator means, and a fourth plurality of pulleys mounted to said support means, said cable being attached at its other end to said cradle-carriage means, and secured at an intermediate point thereof to said take-up pulley.

11. The x-ray table of claim 10, wherein said cable means is fastened at an intermediate point along its length to said take-up pulley so as to avoid slippage.

* * * * *